(12) United States Patent
Ejiri et al.

(10) Patent No.: US 12,329,490 B2
(45) Date of Patent: Jun. 17, 2025

(54) CONVERSION ADAPTER

(71) Applicant: Murata Manufacturing Co., Ltd., Nagaokakyo (JP)

(72) Inventors: Kouki Ejiri, Nagaokakyo (JP); Hiroaki Ichikawa, Nagaokakyo (JP); Hidesato Uegaki, Nagaokakyo (JP); Akihiko Shibata, Nagaokakyo (JP); Kiyotaka Asai, Nagaokakyo (JP); Hirofumi Tsuchimoto, Nagaokakyo (JP); Koji Tanaka, Nagaokakyo (JP); Kyoshiro Okude, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 448 days.

(21) Appl. No.: 17/970,034

(22) Filed: Oct. 20, 2022

(65) Prior Publication Data
US 2023/0043532 A1    Feb. 9, 2023

Related U.S. Application Data

(63) Continuation of application No. PCT/JP2021/015580, filed on Apr. 15, 2021.

(30) Foreign Application Priority Data

Apr. 21, 2020 (JP) .................... 2020-075302

(51) Int. Cl.
*A61B 5/00* (2006.01)
*G16H 40/63* (2018.01)
(Continued)

(52) U.S. Cl.
CPC ............. *A61B 5/0015* (2013.01); *H04B 1/40* (2013.01); *H04B 7/15* (2013.01); *G16H 40/63* (2018.01)

(58) Field of Classification Search
CPC ... A61B 5/0015; A61B 5/021; A61B 5/02416; A61B 5/14542; A61B 2562/227;
(Continued)

(56) References Cited

U.S. PATENT DOCUMENTS 11,538,580 B2 * 12/2022 Sloan ................... A61M 5/1723
11,723,558 B2 *  8/2023 Papas ..................... A61M 5/14
                                                              422/534
(Continued)

FOREIGN PATENT DOCUMENTS

CN          102012390 A      4/2011
EP           1265236 A2 * 12/2002   ......... B29C 65/1406
(Continued)

OTHER PUBLICATIONS

International Search Report in PCT/JP2021/015580, mailed Jul. 6, 2021, 3 pages.

*Primary Examiner* — Mahendra R Patel
(74) *Attorney, Agent, or Firm* — ArentFox Schiff LLP

(57) ABSTRACT

A conversion adapter is provided that includes a radio communication unit that receives biological information based on digital data transmitted from an external biological sensor by radio communication; a converter that converts the biological information based on the digital data received by the radio communication unit to biological information based on analog data; a connection unit that is connectable through wire to an external biological information monitor and that outputs the biological information based on the analog data converted by the converter; a power supply unit that supplies power to the radio communication unit and the converter; an operation input that receives operation performed by a user; and a body part provided with the connection unit and the operation part.

19 Claims, 22 Drawing Sheets

(51) Int. Cl.
*H04B 1/40* (2015.01)
*H04B 7/15* (2006.01)

(58) Field of Classification Search
CPC . A61B 5/0008; A61B 5/002; A61B 2560/045; H04B 1/40; H04B 7/15; G16H 40/63
USPC .......................................................... 455/419
See application file for complete search history.

(56) References Cited

U.S. PATENT DOCUMENTS

| | | | | |
|---|---|---|---|---|
| 12,040,067 | B2 * | 7/2024 | Doniger | G16H 20/17 |
| 2004/0249999 | A1 * | 12/2004 | Connolly | G16H 10/40 |
| | | | | 710/33 |
| 2006/0122542 | A1 * | 6/2006 | Smith | A61B 5/0002 |
| | | | | 600/595 |
| 2010/0328870 | A1 * | 12/2010 | Nakamura | G06F 1/1698 |
| | | | | 361/679.4 |
| 2014/0125495 | A1 * | 5/2014 | Al-Ali | A61B 5/7475 |
| | | | | 340/870.07 |
| 2016/0151008 | A1 * | 6/2016 | Tateda | A61B 5/14552 |
| | | | | 600/476 |
| 2017/0055851 | A1 | 3/2017 | Al-Ali | |
| 2018/0369689 | A1 * | 12/2018 | Murata | A63F 13/235 |
| 2019/0282095 | A1 * | 9/2019 | Bedingham | A61B 90/98 |

FOREIGN PATENT DOCUMENTS

| | | | | | |
|---|---|---|---|---|---|
| EP | 3025646 | A1 | * | 6/2016 | ......... A61B 5/02416 |
| JP | 2006522346 | A | | 9/2006 | |
| JP | 2007215582 | A | | 8/2007 | |
| JP | 2007244516 | A | * | 9/2007 | ............. G06F 19/00 |
| JP | 2016052357 | A | * | 4/2016 | ............... G01T 1/17 |
| JP | 2018527996 | A | | 9/2018 | |
| WO | WO-2004090503 | A2 | * | 10/2004 | .......... A61B 5/0002 |
| WO | WO-2005022692 | A2 | * | 3/2005 | ............... A47C 27/081 |
| WO | WO-2012014691 | A1 | * | 2/2012 | ................ A61B 5/01 |
| WO | WO-2015098272 | A1 | * | 7/2015 | ......... A61B 5/02438 |
| WO | WO-2017092169 | A1 | * | 6/2017 | ........... A61B 5/1473 |

* cited by examiner

FIG. 9
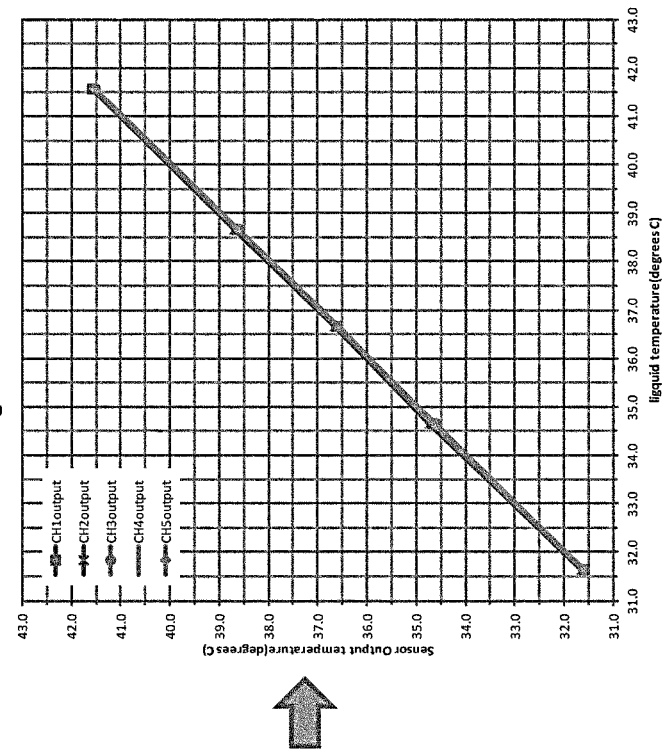
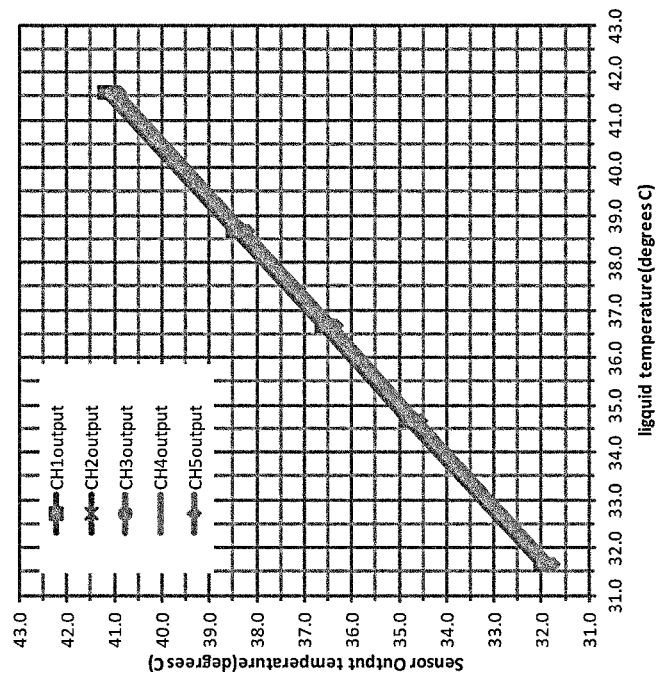

CONVERSION ADAPTER

CROSS REFERENCE TO RELATED APPLICATIONS

This application is a continuation of PCT Application No. PCT/JP2021/015580, filed Apr. 15, 2021, which claims priority to Japanese Patent Application No. 2020-075302, filed Apr. 21, 2020, the entire contents of each of which are hereby incorporated by reference in their entirety.

TECHNICAL FIELD

The present invention relates to a conversion adapter.

BACKGROUND

To date, a biological information monitor (e.g., a bedside monitor) has been used in a hospital (e.g., a sickroom) and the like to monitor the condition of a patient. The patient wears a sensor, such that the biological information monitor monitors, for example, biological information (e.g., vital signs), such as blood pressure, body temperature, respiration, and a pulse rate, of the patient.

Japanese Unexamined Patent Application Publication No. 2007-215582 (hereinafter "Patent Document 1") discloses a wired biological information monitor including a biological sensor connected to the biological information monitor (e.g., bedside monitor) with cables (e.g., through wire). More specifically, the biological information monitor includes a display unit and a plurality of connectors provided in the lower part of the display unit, and the cables with sensors are connected to the plurality of respective connectors to monitor biological information.

Japanese Unexamined Patent Application Publication No. 2018-527996 (hereinafter "Patent Document 2") discloses a wireless biological information monitor that includes a wireless sensor for a patient (e.g., a biological sensor) and to which the wireless sensor is connected wirelessly, the wireless sensor wirelessly transmitting biological information to the biological information monitor.

In the biological information monitor described in Patent Document 1 above, the biological sensor worn by a patient and the biological information monitor are connected by using the cables (e.g., through wire), which can cause problems such as restrained movement of the patient due to the cables.

In contrast, with the wireless biological information monitor described in Patent Document 2, the above-described problem can be solved. However, for example, if a hospital or the like using a wired biological information monitor buys a relatively expensive wireless biological information monitor to replace the wired biological information monitor, the increase expense results in a higher burden from a viewpoint of cost.

There has thus been a desire that a wireless capability be added without replacing an existing device, that is, the wired biological-information processing apparatus (such as the biological information monitor). In addition, standalone operability (that is, in a state without connection to the biological-information processing apparatus) without operability deterioration has also been desired.

SUMMARY OF THE INVENTION

Accordingly, it is an object of the present invention to provide a conversion adapter that enables a biological-information processing apparatus (such as a biological information monitor) with wired connection to a biological sensor or another device to be used simply and at low cost as a wireless biological-information processing apparatus (that is, the wireless capability to be added) and to be operated standalone (that is, in a state without connection to the biological-information processing apparatus) without operability deterioration.

Thus, in an exemplary aspect, a conversion adapter is provided that includes a radio communication unit that receives biological information transmitted from an external apparatus by using radio communication; a converter that converts the biological information received by the radio communication unit to biological information processible by an external biological-information processing apparatus; a connection unit that is connectable to the external biological-information processing apparatus and that outputs, to the biological-information processing apparatus, the biological information converted by the converter; a power supply unit that supplies power to the radio communication unit and the converter; an operation input that receives operation performed by a user; and a main body provided with the connection unit and the operation input.

According to the conversion adapter of the exemplary aspect, the biological information transmitted from the external apparatus is received by using radio communication. After being converted to the biological information processible by the external biological-information processing apparatus, the received biological information is output by using the connection unit. Accordingly, a biological-information processing apparatus connected through wire to, for example, an external biological sensor can be used simply and at low cost as a wireless biological-information processing apparatus (that is, the wireless communication capability can be added). Since the conversion adapter also includes the main body, the power supply unit, and the operation input that are described above, operation of the operation input and insertion and removal of the connection unit can be performed with the main body in a hand. The standalone operation (that is, in a state without connection to the biological-information processing apparatus) can thus be performed without operability deterioration.

As the result, according to the exemplary aspects of the present invention, a biological-information processing apparatus (such as a biological information monitor) connected through wire to the biological sensor or another device can be used simply and at low cost as the wireless biological-information processing apparatus (that is, the wireless capability can be added), and standalone operation (that is, in the state without connection to the biological-information processing apparatus) can also be performed without operability deterioration.

BRIEF DESCRIPTION OF DRAWINGS

FIG. 9 illustrates graphs of temperature output characteristics before calibration and temperature output characteristics after the calibration.

DETAILED DESCRIPTION OF EMBODIMENTS

Figure 1:
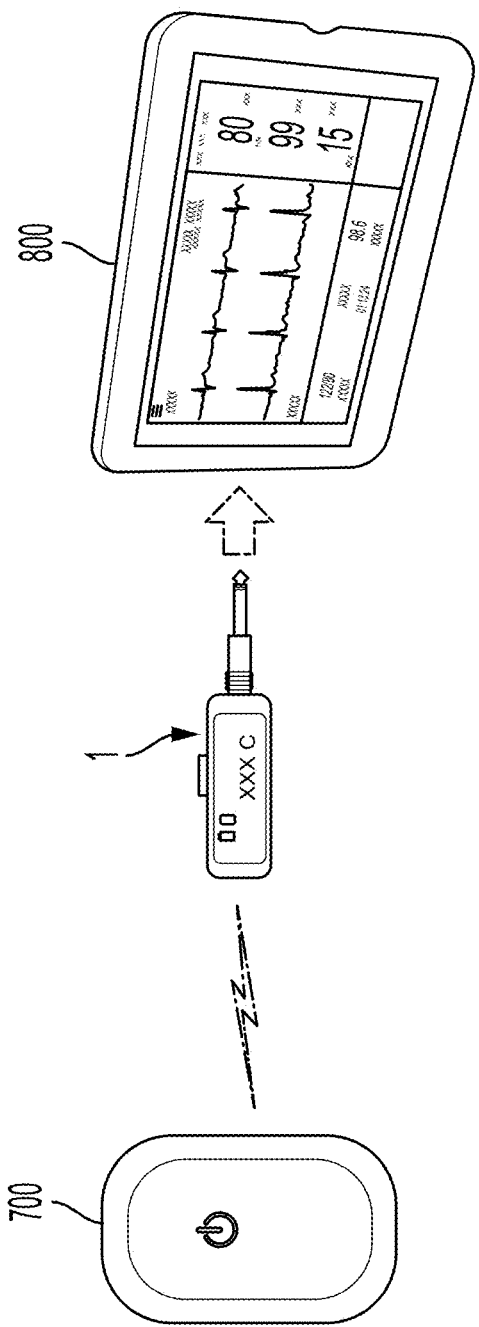
FIG. 1 is a view illustrating respective examples of a conversion adapter according to an exemplary embodiment and a biological information monitor (bedside monitor) to which the conversion adapter is applied.

Hereinafter, an exemplary embodiment of the present invention will be described in detail with reference to the drawings. Note that the same reference numerals are used as those for portions or corresponding portions throughout the drawings. The same components are denoted by the same reference numerals throughout the drawings, and repeated description thereof is omitted.

Figure 2:
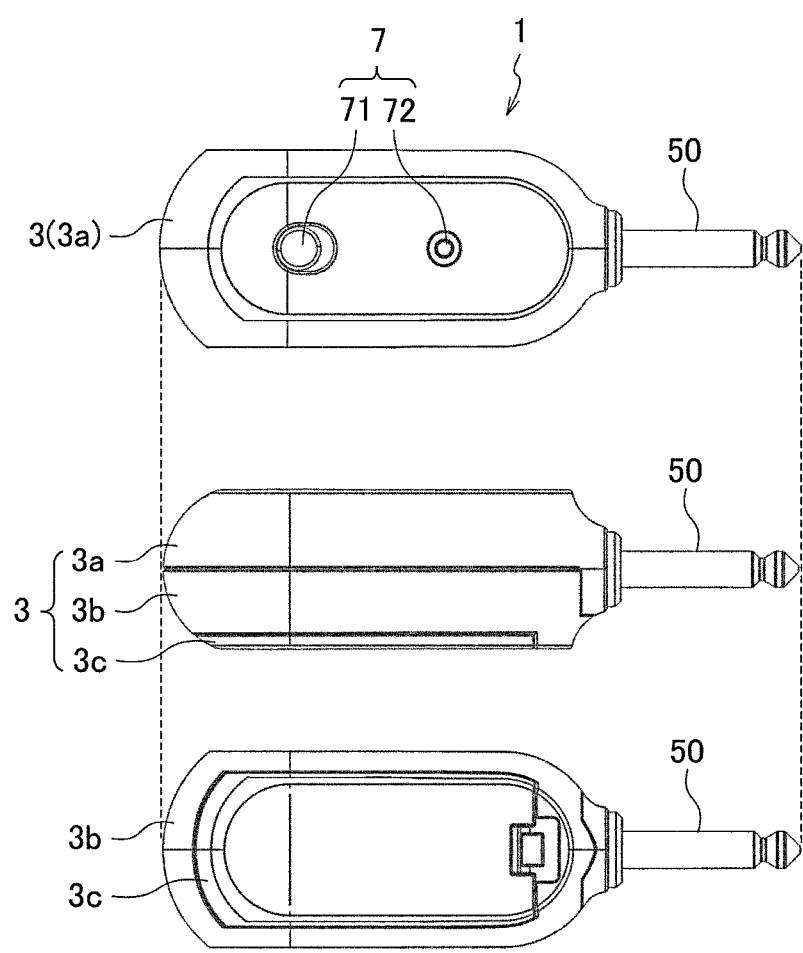
FIG. 2 illustrates a plan view, a side view, and a bottom view illustrating the external appearance of the conversion adapter according to the exemplary embodiment.
Figure 3:
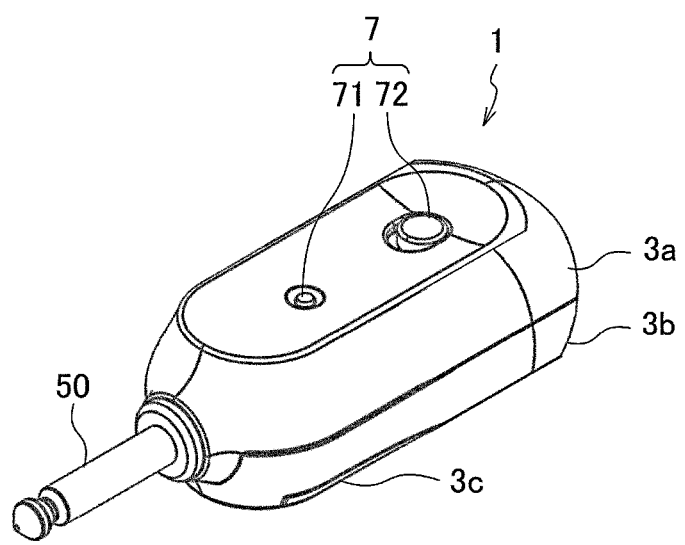
FIG. 3 is a perspective view illustrating the external appearance of the conversion adapter according to the exemplary embodiment.
Figure 4:
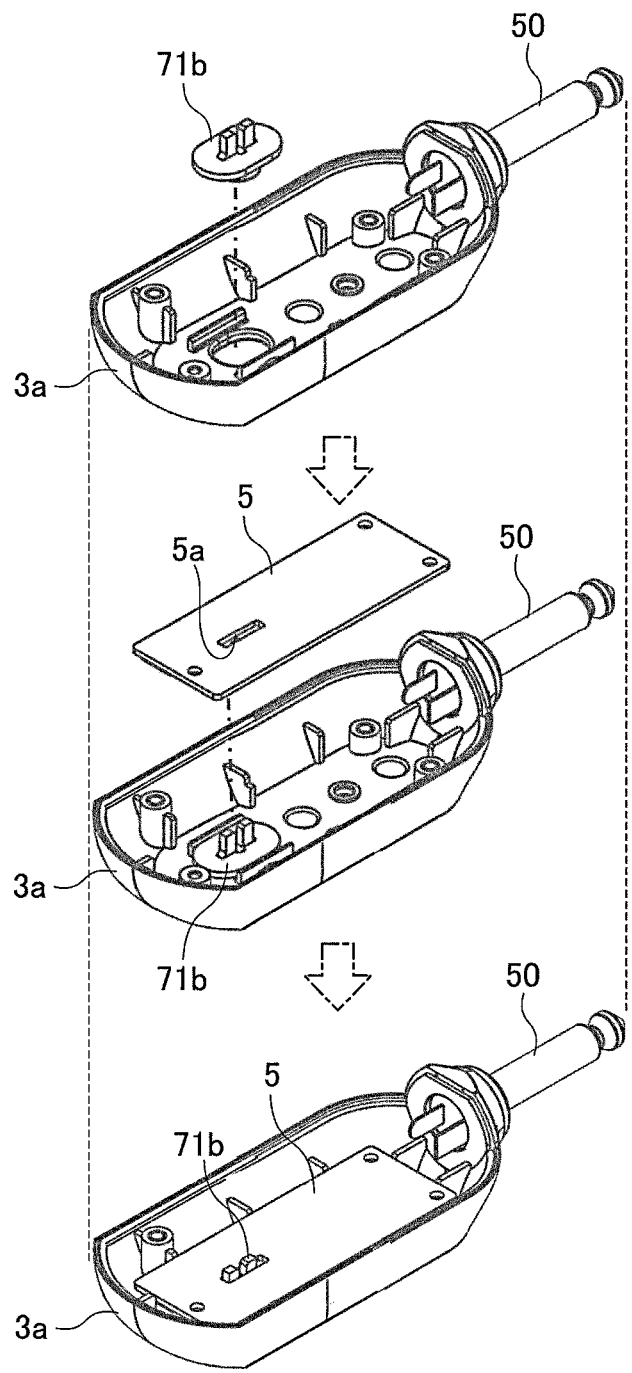
FIG. 4 is a view for explaining how to attach a power supply switch (operation switch).
Figure 5:
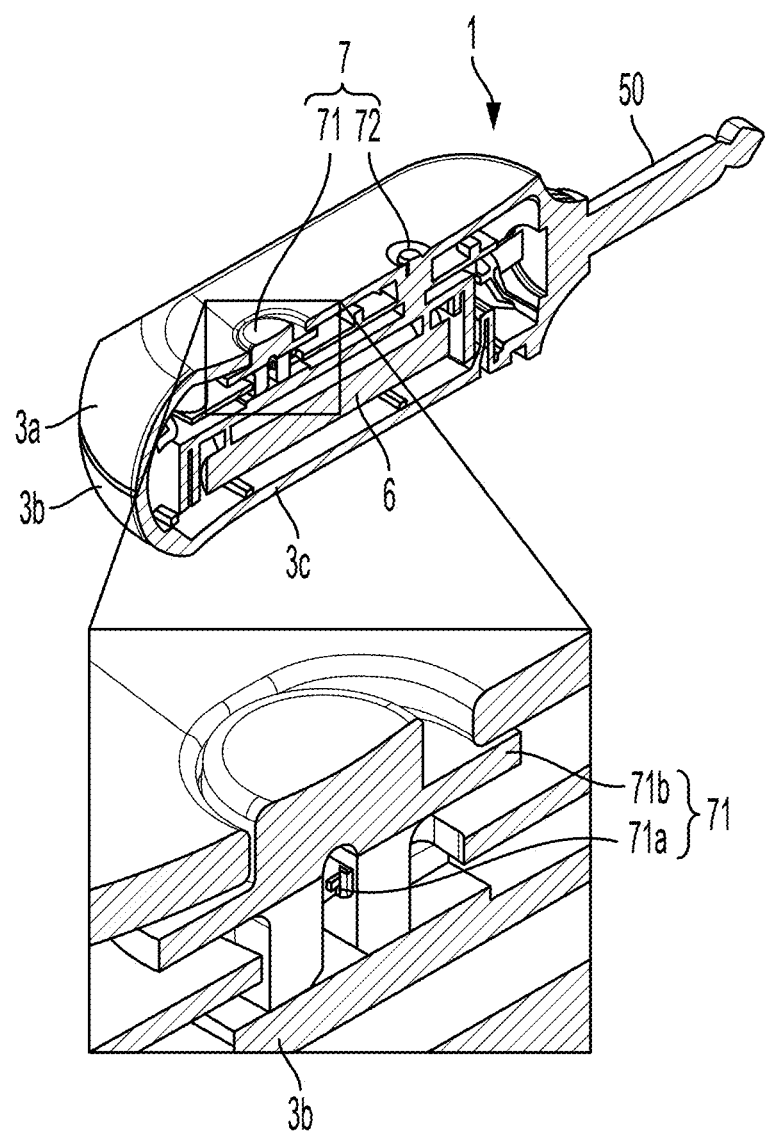
FIG. 5 is a cross-sectional view illustrating a structure in which the power supply switch (operation switch) is attached.
Figure 6:
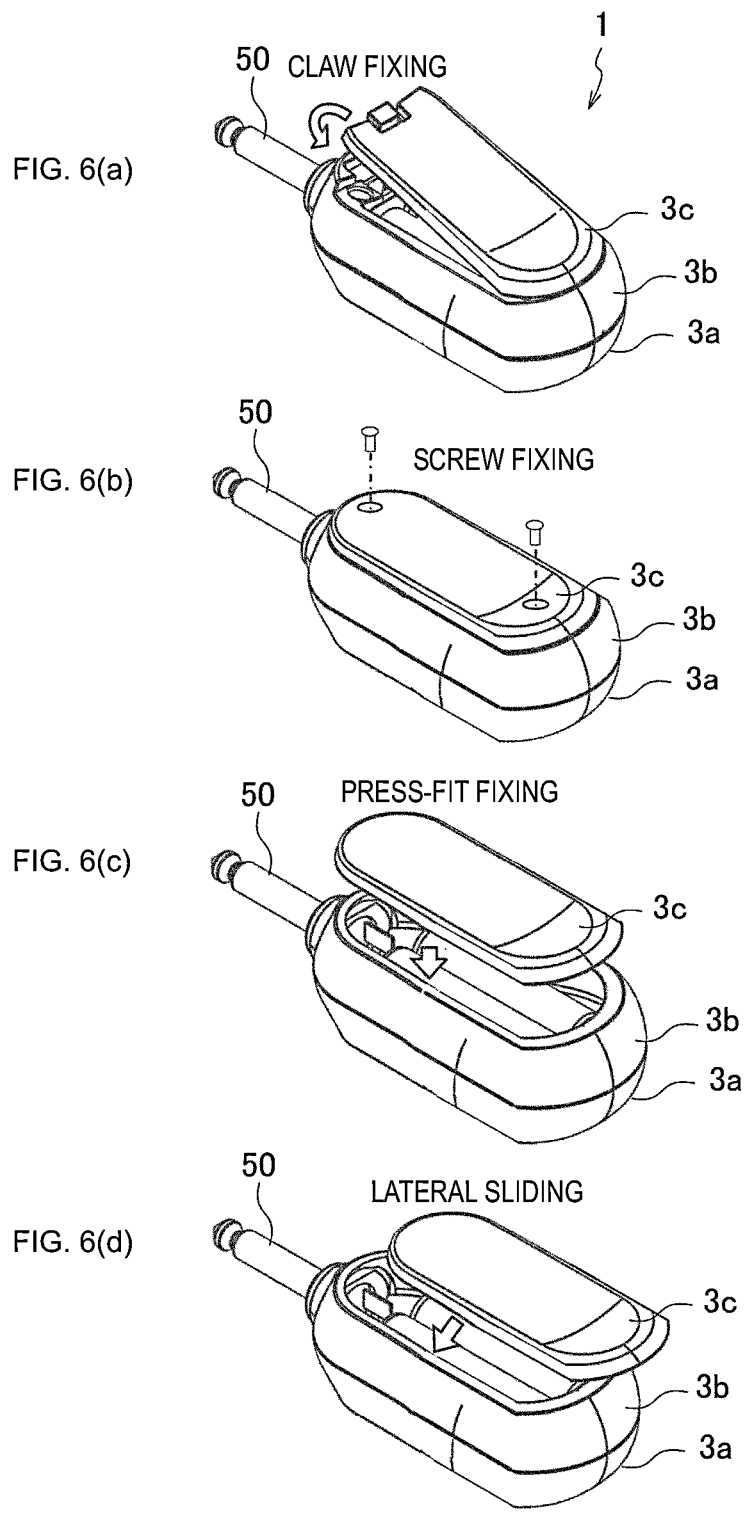
FIGS. 6(*a*) to 6(*d*) are views illustrating an example of how to open and close a back lid.
Figure 7:
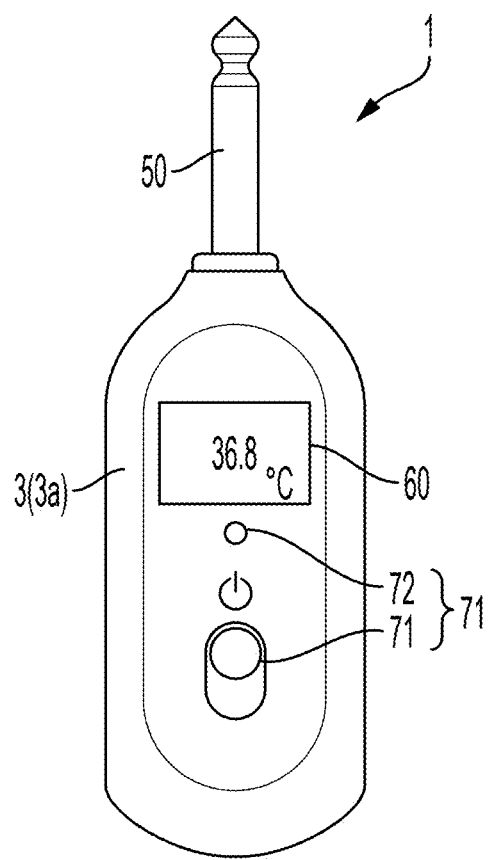
FIG. 7 is a view illustrating an example of a presentation part.
Figure 8:
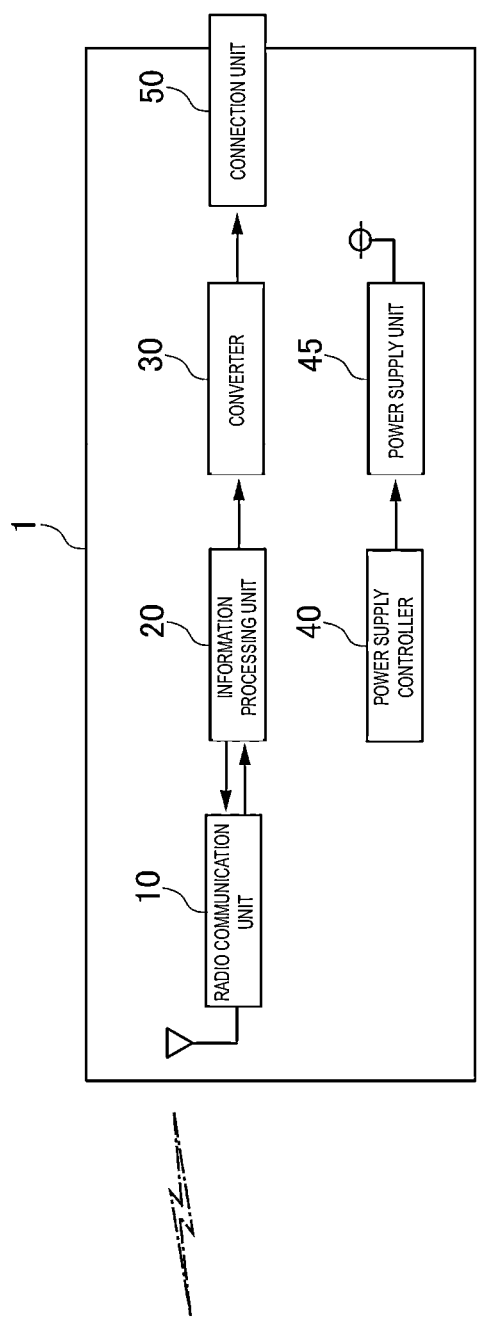
FIG. 8 is a block diagram illustrating the functional configuration of the conversion adapter according to the exemplary embodiment.
Figure 10:
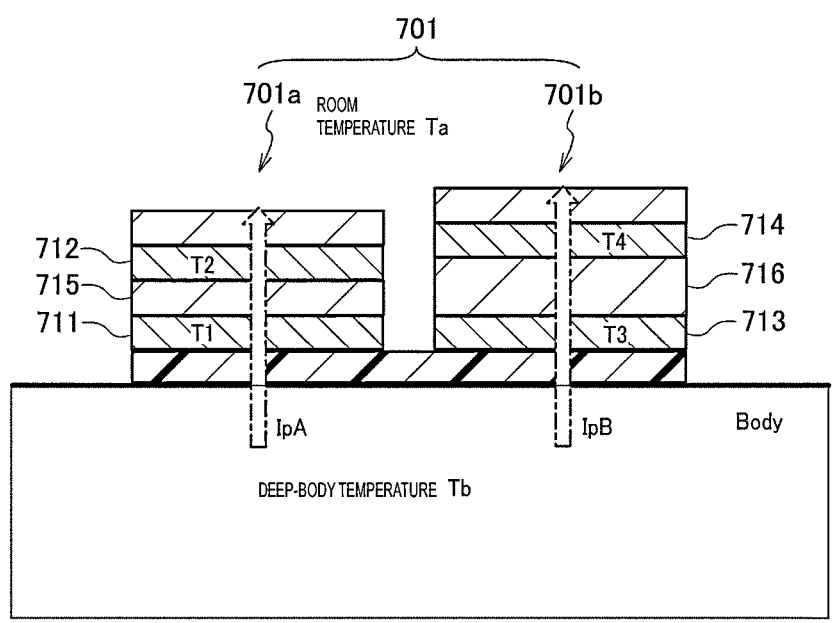
FIG. 10 is a view for explaining a deep-body temperature estimation process.
Figure 11:
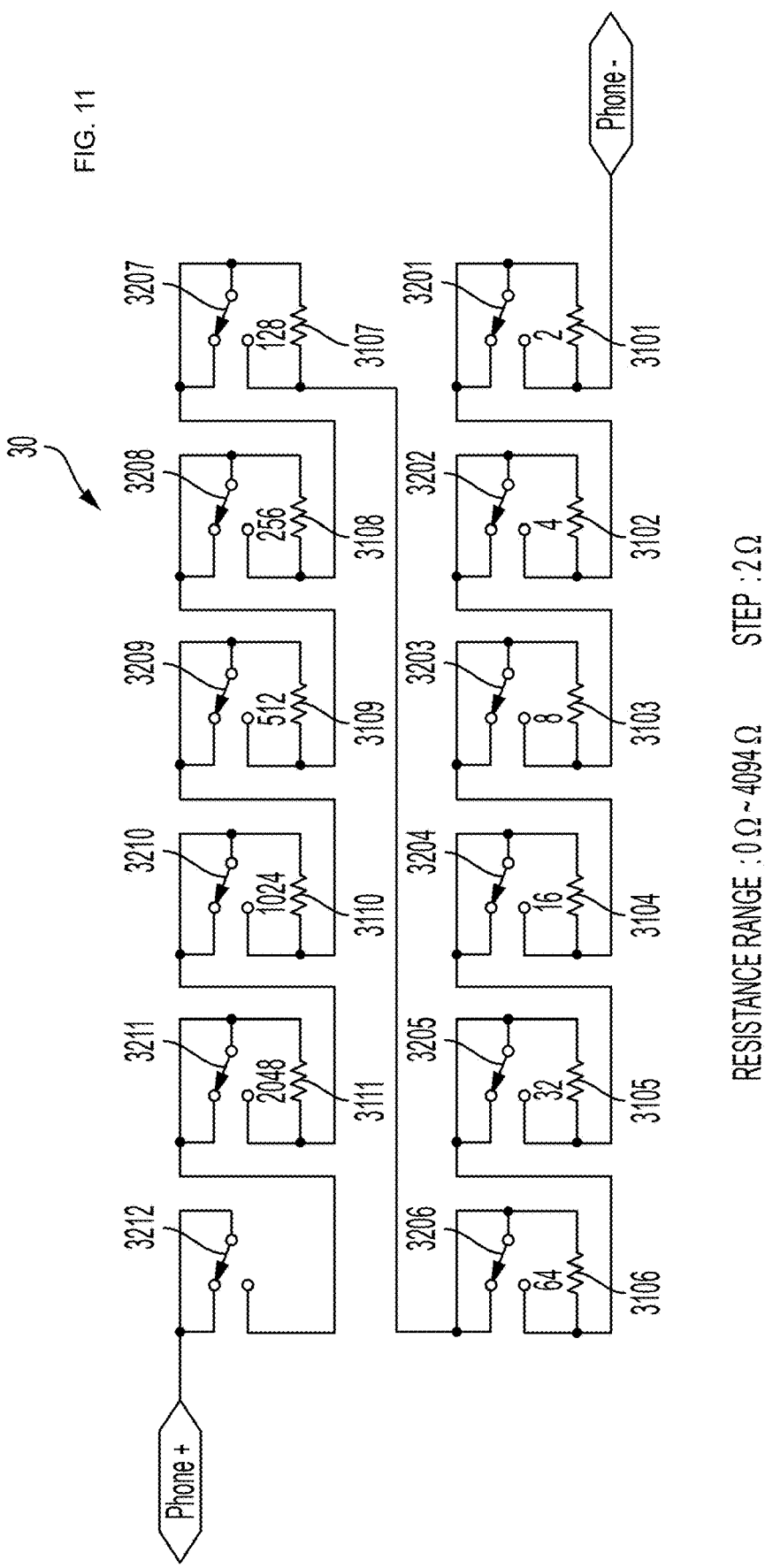
FIG. 11 is a diagram illustrating the configuration of a converter of the conversion adapter according to the exemplary embodiment.
Figure 13:
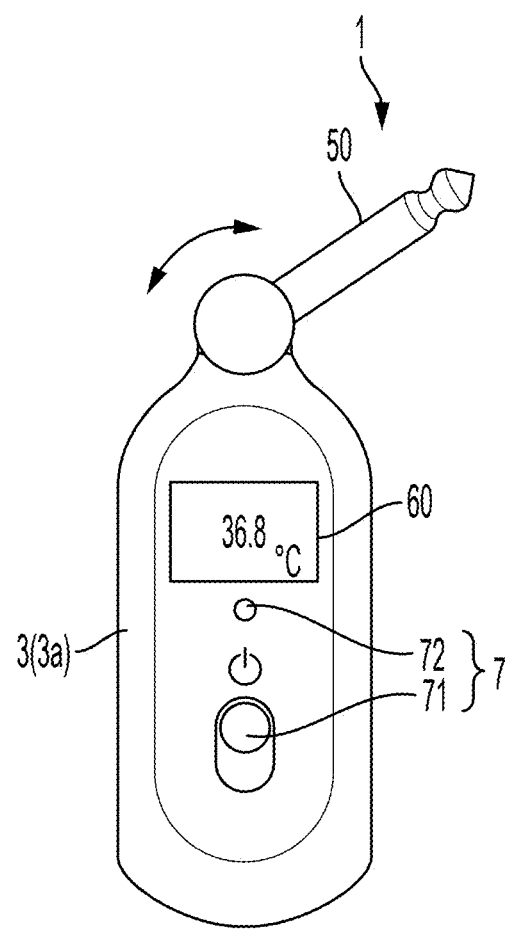
FIG. 13 is a plan view illustrating the external appearance of a conversion adapter according to a first modification of the exemplary embodiment.
Figure 14:
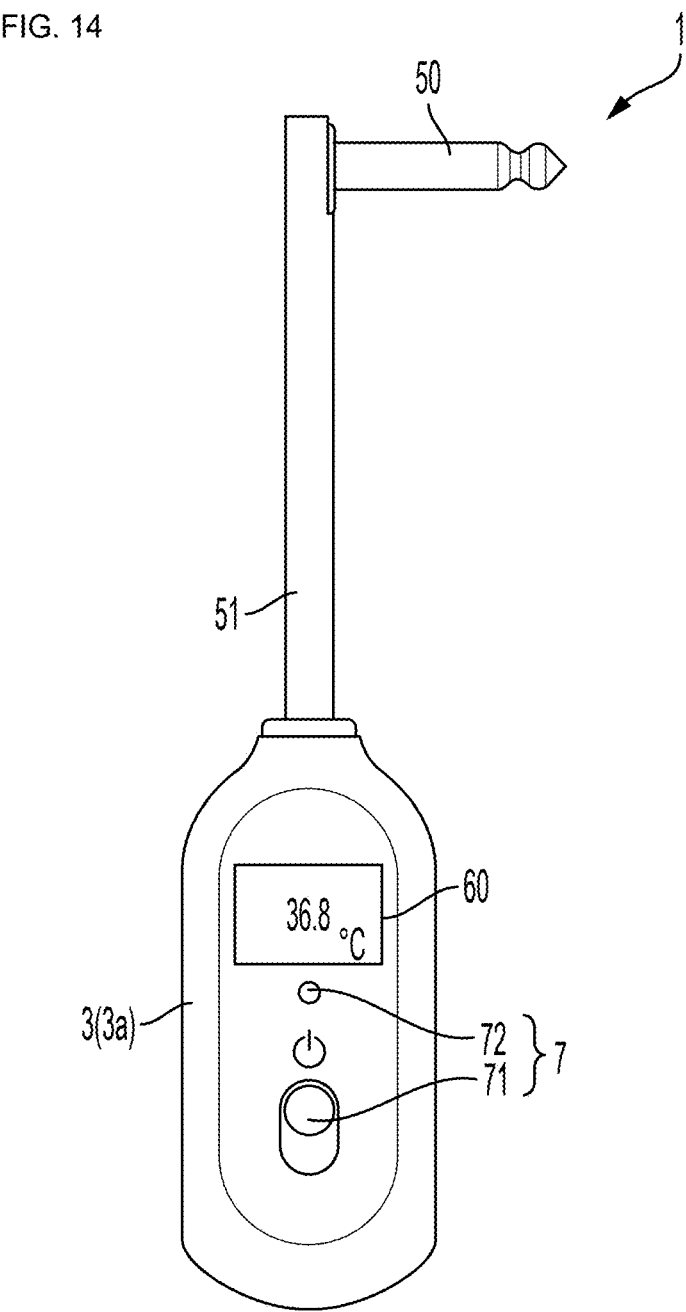
FIG. 14 is a plan view illustrating the external appearance of a conversion adapter according to a second modification of the exemplary embodiment.
Figure 15:
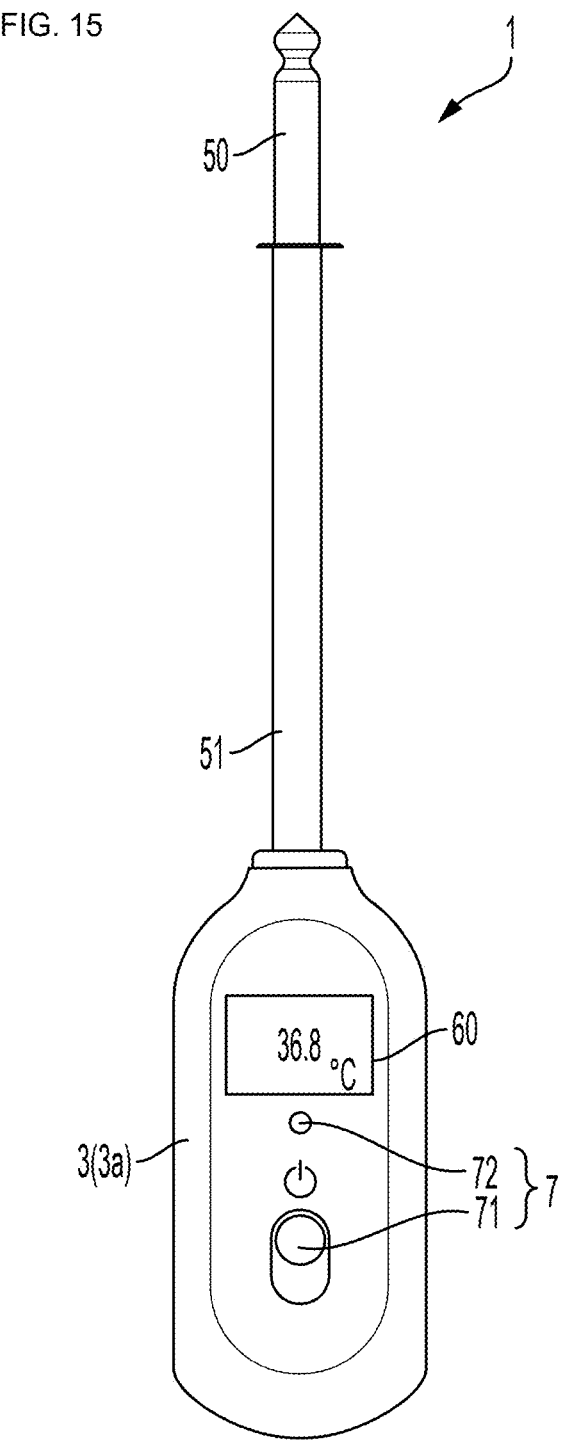
FIG. 15 is a plan view illustrating the external appearance of a conversion adapter according to a third modification of the exemplary embodiment.
Figure 16:
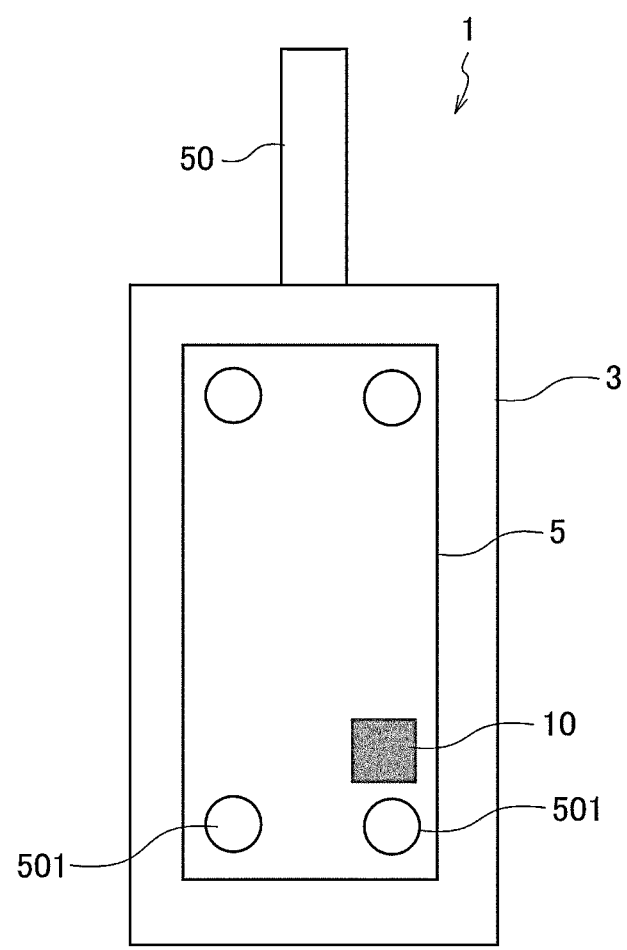
FIG. 16 is a schematic view illustrating an example of a structure in which a circuit board is attached.
Figure 17:
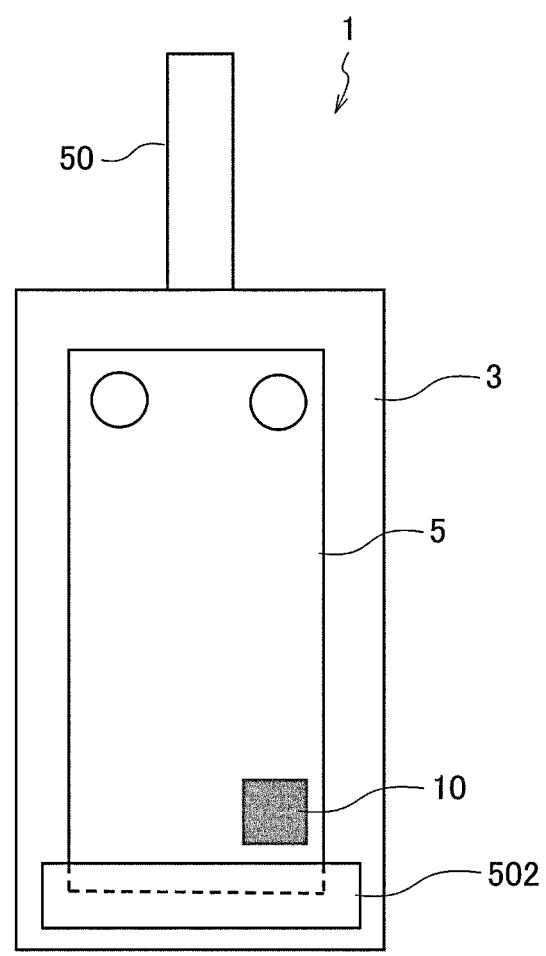
FIG. 17 is a schematic view illustrating another example of the structure in which the circuit board is attached.
Figure 18:
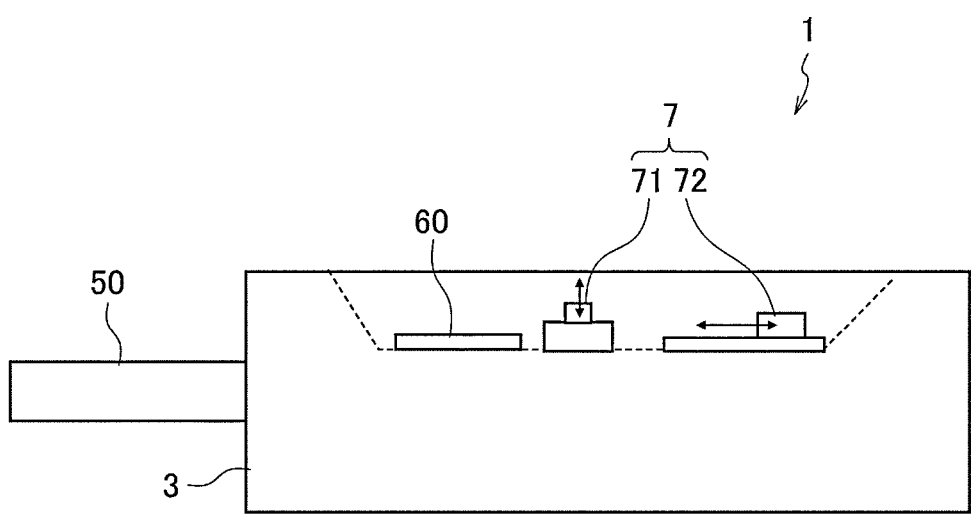
FIG. 18 is a schematic view illustrating a structure in which the operation switch is attached.

First, the configuration of a conversion adapter 1 according to the exemplary embodiment will be described by using FIGS. 1 to 22. FIG. 1 is a view illustrating respective examples of the conversion adapter 1 and a biological information monitor 800 to which the conversion adapter 1 is applied. FIG. 2 is a plan view, a side view, and a bottom view illustrating the external appearance of the conversion adapter 1. FIG. 3 is a perspective view illustrating the external appearance of the conversion adapter 1. FIG. 4 is a view for explaining how to attach a power supply switch 71. FIG. 5 is a cross-sectional view illustrating a structure in which the power supply switch 71 is attached. FIG. 6 is a view illustrating an example of how to open and close the back lid. FIG. 7 is a view illustrating an example of a presentation part 60. FIG. 8 is a block diagram illustrating the functional configuration of the conversion adapter 1. FIG. 11 is a diagram illustrating the configuration of a converter 30 of the conversion adapter 1. FIGS. 13 to 15 are each a plan view illustrating the external appearance of the conversion adapter 1 according to a corresponding one of first to third modifications. FIGS. 16 and 17 are each a schematic view of an example of a structure in which a circuit board 5 is attached. FIG. 18 is a schematic view illustrating a structure in which the operation switch is attached. FIGS. 19 to 22 are each a schematic view illustrating a corresponding one of first to fourth examples of a fixing member.

In general, the conversion adapter 1 is a conversion device configured to connect a wireless biological sensor 700 to the wired biological information monitor (e.g., a bedside monitor) 800. The conversion adapter 1 enables the connection therebetween by absorbing a difference in standard, voltage, and the like between the wireless biological sensor 700 and the wired biological information monitor 800. It is noted that the details will be described later.

The biological sensor 700 is an attached biological sensor that is worn by a measurement target (for example, a patient in hospital) and that detects biological information from the measurement target. As the biological information, for example, body temperature, blood pressure, a blood sugar level, oxygen saturation, a heart rate, ECG, and PPG can be cited. Any of various biological sensors (such as a body temperature sensor, a photoplethysmographic sensor, a pressure sensor, a blood sugar level sensor, an oxygen saturation sensor, a pulse wave sensor, and an electrocardiographic electrode) that detect (e.g., acquire) these pieces of biological information is thus used as the biological sensor 700. In this embodiment, a case where a temperature sensor using a thermistor having a resistance value that varies depending on the temperature is used as the biological sensor 700 will be described as an example.

According to the exemplary aspect, the biological sensor 700 includes an A/D converter that converts an analog signal (i.e., the biological signal) to digital data. That is, the biological sensor 700 is configured to convert a detected biological signal to digital data (i.e., the biological information). The biological sensor 700 also includes a radio communication module and wirelessly transmits the digital data subjected to the A/D conversion. Note that the digital data (i.e., the biological information) can be a physical quantity such as temperature or a pressure and can also be waveform data such as an electrocardiogram. For the radio communication, radio communication methods (e.g., radio communication standards) such as Bluetooth® low energy (BLE), WiFi, long term evolution (LTE), and Sub-GHz (a 900 MHz band) can be used. In addition, radio communication methods (radio communication standards), such as near field communication (NFC) (ISO/IEC 18092) and MIFARE® (ISO/IEC 14443), can also be used.

For the biological information monitor (corresponding to a biological-information processing apparatus for purposes of this disclosure) 800, a publicly known wired and analog-input biological information monitor can be used. The biological information monitor 800 includes a display screen and receives and displays the biological information that is detected, converted, and transmitted by the biological sensor 700 and that is received, converted, and relayed via the conversion adapter 1, as described in detail below.

As described above, the conversion adapter 1 is the conversion device used to wirelessly connect the wireless biological sensor 700 to the wired biological information monitor 800. The conversion adapter 1 enables the connection therebetween by absorbing a difference in standard, voltage, and the like, between the wireless biological sensor 700 and the wired biological information monitor 800. In particular, the conversion adapter 1 is configured to enable the wired biological information monitor 800 to be used simply and at low cost as a wireless biological information monitor (that is, a wireless capability to be added) and to be operated standalone (that is, in a state without connection to the biological information monitor) without operability deterioration.

Accordingly, the conversion adapter 1 mainly includes a body part 3 (e.g., a main body), the circuit board 5, an operation input or control 7 (e.g., the power supply switch 71 and a communication switch 72), a radio communication unit 10, an information processing unit 20, the converter 30, a power supply controller 40, a power supply unit (e.g., power supply circuit) 45, a connection unit 50, and the presentation part 60.

The body part 3 is the enclosure, such as a case, of the conversion adapter 1 and mainly includes an upper case 3a and a lower case 3b that result from division into two, that is, upper and lower parts, and an operable and closable back lid 3c. As further shown, the body part 3 has the connection unit 50 (described in detail later) protruding from an end portion thereof. In addition, the operation input 7 is provided on the upper surface (e.g., a top surface) of the body part 3 (e.g., upper case 3a). A user can operate the operation input 7 (the power supply switch 71 and the communication switch 72) and insert and remove the connection unit 50, with the body part 3 in their hand. Note that the exterior of the body part 3 (the upper case 3a and the lower case 3b) is preferably formed from, for example, a crystalline material (such as PP, POM, or PBT). This is because resistance to ethanol, hypochlorous acid, and the like used in a health care site is to be increased.

For easy holding (such as pinching), the body part 3 is formed in such a manner that at least part of (an upper surface and a lower surface in this embodiment) of the outer surface is formed to curve concavely (that is, concaved to curve). As illustrated in FIG. 18, the operation input 7 (the power supply switch 71 and the communication switch 72) (described later) is located near substantially the center of the concaved surface. Accordingly, the operation input 7 (the power supply switch 71 and the communication switch 72) does not protrude from the body part 3, and thus wrong operation can be prevented. In addition, the power supply switch 71, the communication switch 72, and other components can be prevented from damaged, for example, at the time of falling.

The circuit board 5 (described later) is mounted inside the body part 3, and a battery 6 that supplies power is accommodated therein. The body part 3 has the operable and closable back lid 3c (corresponding to an opening and closing part for purposes of this disclosure) to replace the battery 6. To prevent the back lid 3c from opening or closing wrongly at the time of inserting or removing the conversion adapter 1 (connection unit 50), the opening and closing directions (opening and closing operation directions) of the back lid 3c are set to be different from the inserting and removing directions (axial directions) of the connection unit 50. More specifically, as illustrated in FIGS. 6(a) to (d), methods such as claw fixing by turning (see FIG. 6(a)), screw fixing (see FIG. 6(b)), press-fit fixing using a packing (see FIG. 6(c)), and lateral sliding (see FIG. 6(d)) are employed as opening and closing the back lid 3c.

The operation input 7 includes a plurality of operation switches that receive operation performed by a user, that is, the power supply switch 71 and the communication switch 72 in this embodiment. To sense a difference between the switches and prevent a wrong operation, the power supply switch 71 and the communication switch 72 are different from each other in at least one of, for example, an operation method, a size (e.g., dimensions), or a shape. For example, in this embodiment, a slide switch is used as the power supply switch 71, and a push-button switch is used as the communication switch 72. The size (e.g., dimensions) of the power supply switch 71 is set larger than that of the communication switch 72 in an exemplary aspect.

As described above, at least part (the upper surface and the lower surface in this embodiment) of the outer surface is formed to curve concavely in the body part 3, and the operation input 7 (the power supply switch 71 and the communication switch 72) is located near substantially the center of the concaved surface. Accordingly, the operation input 7 (the power supply switch 71 and the communication switch 72) does not protrude from the body part 3, and thus wrong operation can be prevented. In addition, locating the operation input 7 in the central portion enables the visibility and the operability to be improved.

A structure in which the power supply switch 71 is attached will be described with reference to FIGS. 4 and 5. First, a rectangular through-hole 5a extending in a thickness direction of the circuit board 5 is formed in the circuit board 5 mounted inside the body part 3. A switch cover 71b including a pair of protruding portions formed parallel to each other is attached to the upper surface (top surface) of the body part 3 (upper case 3a) in such a manner as to slide freely. In contrast, the body of the power supply switch 71 is soldered on the main surface (component side) of the circuit board 5. The power supply switch 71 is mounted on the circuit board 5 in such a manner that a slidable movable switch (contact point) part 71a protrudes parallel to the main surface of the circuit board 5. Moreover, the switch cover 71b is attached in the following manner. The pair of protruding portions extend in a direction perpendicular to the main surface of the circuit board 5, and protrude (from the back surface) through the through-hole 5a in the circuit board 5, the tip ends of the protruding portions abut on the inner side of the lower surface of the body part 3 (that is, the inner side of the lower case 3b), and the movable switch part 71a of the power supply switch 71 is engaged between the pair of protruding portions.

In the exemplary aspect, sliding the switch cover 71b enables the power supply switch 71 to be turned on or off. In addition, a pressing force (e.g., a load) applied to the switch cover 71b can be received by the lower case 3b, not by the circuit board 5 or the power supply switch 71, and thus the circuit board 5 and the power supply switch 71 can be prevented from being damaged. In addition, when the power supply switch 71 is assembled, whether the pair of protruding portions of the switch cover 71b are appropriately engaged with the movable switch part 71a can be verified through the through-hole 5a in the circuit board 5.

As illustrated in FIG. 7, the presentation part 60 visually and auditorily presents, for example, biological information, operation information regarding the operation input 7 (the power supply switch 71 and the communication switch 72), a radio connection state, and the state of the biological sensor 700. More specifically, as illustrated in FIG. 7, the presentation part 60 has, for example, a liquid crystal display, a seven-segment LED, and the like and displays deep-body temperature (for example, in response to the pressing of the communication switch 72, deep-body temperature is displayed for 15 seconds) and error information in response to the occurrence of an error (for example, "EXX (XX is an error code)") is displayed. Moreover, the presentation part 60 displays warning information indicating that the remaining life of the battery 6 is low (lower than or equal to a predetermined amount). Note that in addition to or instead of the displaying above, the information may be presented by sound. This configuration enables the user to verify, for example, an operation state and an information processing state and know error information and warning information, by using the conversion adapter 1 alone.

The radio communication unit 10 illustrated in FIG. 8 receives, from the external biological sensor 700, the biological information based on the digital data transmitted by using radio communication. For example, the radio communication unit 10 receives a plurality of pieces of temperature information and the like as the biological information. For the radio communication unit 10, a radio communication method (radio communication standard) such as Bluetooth® low energy (BLE), WiFi, long term evolution (LTE), or Sub-GHz (a 900 MHz band) can be used to suit the radio communication method for the biological sensor 700 described above. Alternatively, a radio communication method (radio communication standard), such as near field communication (NFC) (ISO/IEC 18092) or MIFARE® (ISO/IEC 14443), can also be used. To avoid an influence of the metal connection unit 50 and the like (such as the deterioration of an antenna radiation efficiency), the radio communication unit 10 is provided inside the body part 3 on the other end portion side (on an opposite end portion of the body part 3 from the connection unit 50). To avoid an influence of a metal, the circuit board 5 is preferably fixed with resin screws 501 near the radio communication unit 10, instead of metal screws, as illustrated in FIG. 16. Alternatively, as illustrated in FIG. 17, a configuration in which the circuit board 5 is pressed against the portion near the radio communication unit 10 by using a rib 502 on the exterior may be employed.

The radio communication unit 10 is preferably configured to transmit information to an external medical apparatus by using radio communication. More specifically, for example, a configuration enabling the biological information processed and generated by the information processing unit 20 to be transmitted to a different medical apparatus (such as an electric medical record system) having a radio receiving function via the radio communication unit 10 is preferably employed. The configuration as described above enables the biological information processed and generated by the conversion adapter 1 to be transmitted to the different medical apparatus. The conversion adapter 1 can also be used as an operation terminal.

Likewise, the radio communication unit 10 is preferably configured to transmit, to the biological sensor 700, information (for example, verification information regarding connection with the biological sensor 700) by using radio communication. In this case, for example, pressing the communication switch 72 causes a connection verification command to be transmitted and the LED of the biological sensor 700 connected (e.g., paired) wirelessly to light up or blink. Note that instead of the lighting or blinking of the LED, the biological sensor 700 may vibrate or sound a buzzer. According to the configuration as above, if there are a plurality of biological sensors 700, the light emitting, the sound generation, or the like on the biological sensor 700 side in response to receiving the connection verification information enables a connection target to be verified. It is noted that the biological information received by the radio communication unit 10 is output to the information processing unit 20.

The information processing unit 20 includes a micro control unit (MCU) or the like. The information processing unit 20 is configured to perform data processing of the biological information based on the digital data received by the radio communication unit 10 and generates significant data to be displayed and used by the biological information monitor 800.

In particular, the information processing unit 20 can be configured to perform an algorithmic process on the biological information based on the digital data. In this embodiment, in the algorithmic process, for example, a calibration process for correcting individual variation of the biological sensor 700, a deep-body temperature estimation process for estimating deep-body temperature based on a plurality of pieces of temperature information, and a balance determination process for determining whether the biological sensor 700 (temperature sensor) is thermally balanced (in a state without heat flow rate variation) are performed. The processes will herein be described.

First, as illustrated in FIG. 9, the information processing unit 20 converts a digital value x to temperature data Y by using the fitting curve "$Y=ax^2+bx+c$". At this time, the voltage output for each temperature is output as an offset difference due to the influence of characteristic variation (e.g., an individual variation) and the like in thermistors. The information processing unit 20 thus performs a calibration process for correcting the characteristic variation (e.g., an individual variation) of the biological sensor 700. More specifically, as illustrated in FIG. 9, the c constant of the fitting curve is calibrated for each individual, and the influence of the variation due to an individual difference is thereby reduced. Note that FIG. 9 illustrates graphs of the temperature output characteristics before the calibration (i.e., the left graph) and the temperature output characteristics after the calibration (i.e., the right graph). The horizontal axis in FIG. 9 represents temperature (° C.), and the vertical axis represents value (digital value) resulting from the digital conversion of output voltages (partial pressure values) of the biological sensor 700 (thermistors). In the calibration, a polynomial is calculated after temperature characteristics (temperature—digital output) are measured in a state where digital output value variation in UART output is reduced due to power supply from a DC power supply, and the c constant is obtained such that a digital value at 37° C. matches the actual measured temperature. At this time, the c constant is obtained by using the mean value of inclinations a, b of, for example, five (CH1 to CH5) temperature sensors. The curve fitting and the offset value per individual (c constant) that are thus obtained are stored as the calibration information in the EEPRROM or the like, and temperature output with a small deviation (±0.05° C.) from the reference (e.g., a platinum thermometer) is obtained (see the right graph in FIG. 9).

The information processing unit 20 is also configured to estimate deep-body temperature based on the plurality of pieces of temperature information. FIG. 10 is a view for explaining a deep-body temperature estimation process. The information processing unit 20 obtains body temperature data, such as deep-body temperature, based on a thermal resistance value RpA of a thermal resistance element 715 that is stored in advance, a detected temperature T1 of a first temperature sensor 711, a detected temperature T2 of a second temperature sensor 712, a thermal resistance value RpB of a thermal resistance element 716 that is stored in advance, a detected temperature T3 of a third temperature sensor 713, and a detected temperature T4 of a fourth temperature sensor 714.

More specifically, by using the following formulas (1) and (2), the information processing unit 20 compares heat flows in two systems having different thermal resistance elements (e.g., thermal resistances), erases an unknown thermal resistance RB, and calculates and/or estimates a body-temperature data candidate Tb of a user (e.g., a human body) having the unknown thermal resistance RB.

$$\text{Heat flow } IpA=(T1-T2)/RpA=(Tb-T1)/RB \tag{1}$$

$$\text{Heat flow } IpB=(T3-T4)/RpB=(Tb-T3)/RB \tag{2}$$

RpA and RpB denote the thermal resistances (known) of the thermal resistance elements 715 and 716.

If the thermal resistance RB of the user is known, a body-temperature data candidate can be calculated and/or estimated by using one of sensing parts, that is, a sensing part 701a (or 701b). In more detail, in a case where the body-temperature data candidate of the human body is Tb, the detected temperature of the first temperature sensor 711 is T1, the detected temperature of the second temperature sensor 712 is T2, an equivalent thermal resistance from the deep part of the human body to the surface is RB, and an equivalent thermal resistance of the thickness direction of the thermal resistance element 715 is RpA, the body-temperature data candidate Tb that reaches a thermally balanced state can be expressed as in the following formula (3).

$$Tb=T2+\{RpA/(RB+RpA)\}(T1-T2) \tag{3}$$

Thus, in the case where the thermal resistance RB of the human body is known, or by setting, for example, a typical or standard thermal resistance value as the thermal resistance RB of the human body, a deep-body temperature Tb can be obtained from the temperature T1 detected by the first temperature sensor 711 and the temperature T2 detected by the second temperature sensor 712.

When obtaining the deep-body temperature Tb, the information processing unit 20 acquires the body temperature data based on temperature data detected when it is determined that the biological sensor 700 is thermally balanced. The information processing unit 20 determines whether the biological sensor 700 (e.g., the temperature sensors) is thermally balanced (in a state without heat flow rate variation) by using a balanced-state discrimination formula. More specifically, the information processing unit 20 determines whether the biological sensor 700 (temperature sensors) is thermally balanced by using the following balanced-state discrimination formula (4). That is, in a case where the temperature data detected by the first temperature sensor 711 is T1, the temperature data detected by the second temperature sensor 712 is T2, the temperature data detected by the third temperature sensor 713 is T3, the temperature data detected by the fourth temperature sensor 714 is T4, and if the balanced-state discrimination formula (4) is satisfied, the information processing unit 20 determines that the biological sensor 700 is thermally balanced. In contrast, if the balanced-state discrimination formula (4) is not satisfied, the information processing unit 20 determines that the biological sensor 700 is not thermally balanced (not balanced).

$$T3-T4>T1-T2, T3>T1 \tag{4}$$

It is noted that if a room temperature Ta in the hospital can be acquired from, for example, an electric medical record system (or an infection management system), whether a temperature detection part 701 (e.g., the four temperature sensors 711 to 714) is thermally balanced may be determined further in consideration for the balanced-state discrimination formulas (5), (6), and (7). In this case, if the balanced-state discrimination formulas (5), (6), and (7) in addition to the balanced-state discrimination formula (4) above are all satisfied, it is determined that the biological sensor 700 is thermally balanced. In contrast, if any one or all of the balanced-state discrimination formulas (4) to (7) are not satisfied, it is determined that the biological sensor 700 is not thermally balanced (not balanced).

$$dTa>dT4 \tag{5}$$

$$K(T1-T2)-(T3-T4)>0(\text{when } Ta>Tb) \tag{6}$$

$$K(T1-T2)-(T3-T4)\leq0(\text{when } Ta\leq Tb) \tag{7}$$

A constant K is a ratio of the thermal resistances in the two heat flows.

Thereafter (that is, after the processes described above), the information processing unit 20 converts the biological information (i.e., the biological data) obtained in the processes described above to a digital value corresponding to an analog amount for the biological information monitor 800. The conversion can be performed based on, for example, a transformation or a reference table. The biological information based on the digital data processed by the information processing unit 20 is output to the converter 30.

The converter 30 converts the biological information based on the digital data processed by the information processing unit 20 to the biological information (signal) based on analog data processible by the biological information monitor 800. For example, the converter 30 converts the biological information (i.e., the digital value) to a resistance value corresponding to the resistance value (i.e., the analog data) of the thermistors, such as biological sensor 700. Note that the analog amount is not limited to the resistance value and may be, for example, a current value or a voltage value.

The case of the conversion to the resistance value will herein be described as an example. In this case, as illustrated in FIG. 11, the converter 30 includes a plurality of resistors 3101 to 3111 connected in series (11 resistors in the example illustrated in FIG. 11) and switching elements 3201 to 3212 that are respectively connected in parallel to the plurality of resistors 3101 to 3111 and that respectively turn on (enable) and off (disable) the plurality of resistors 3101 to 3111. The respective resistance values of the plurality of (11) resistors 3101 to 3111 are each set at $2^1$ to $2^n\Omega$ (n is a natural number) in an exemplary aspect. In particular, the respective resistance values of the plurality of (11) resistors 3101 to 3111 can thus respectively set at 2, 4, 8, 16, 32, 64, 128, 256, 512, 1024, and 2048 ($\Omega$).

The converter 30 obtains a resistance value (i.e., an analog value) of thermistors corresponding to the biological information (i.e., the digital value) and obtains a combination of the plurality of (11) resistors 3101 to 3111 such that the resistance value of the thermistors corresponding to the obtained biological information matches a combined series resistance value, decides a combination of the turning on and off of the switching elements 3201 to 3212 to achieve the obtained combination of the resistors 3101 to 3111, and turns on or off the switching elements 3201 to 3212. The processing and the control are performed by the MCU. If the resistance value is controlled by the 12 switching elements 3201 to 3212, a deep-body temperature of 37.0° C. leads to, for example, the combination "switching element 3201: ON, switching element 3202: OFF, . . . , switching element 3212:

ON", and a deep-body temperature of 37.5° C. leads to, for example, the combination "switching element 3201: OFF, switching element 3202: ON, . . . , switching element 3212: ON".

Figure 12:
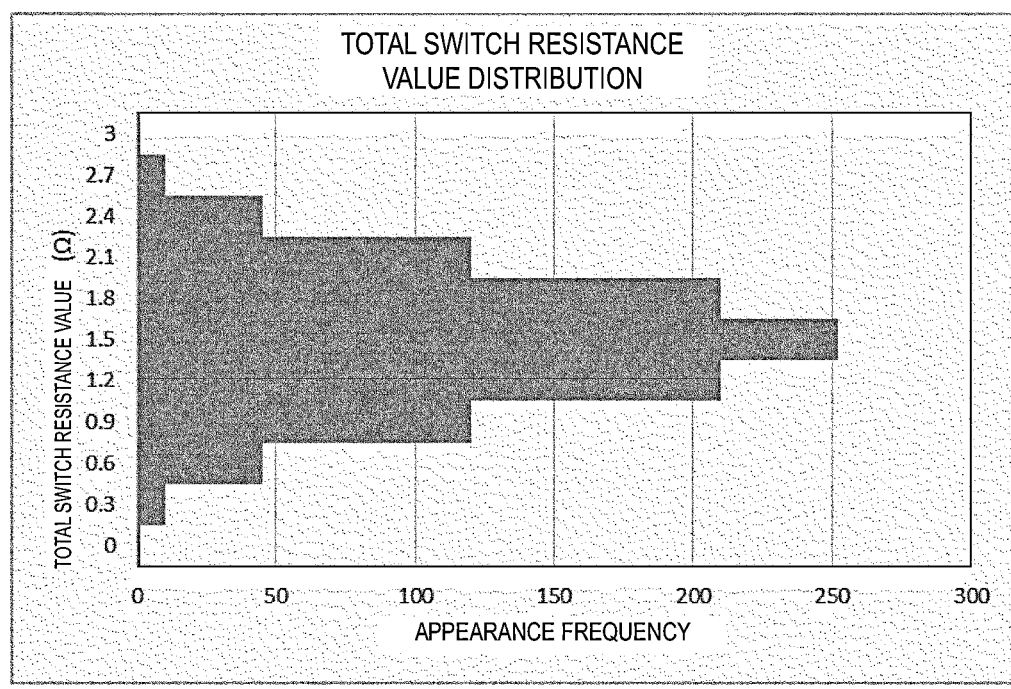
FIG. 12 is a graph illustrating switching resistance distribution of a plurality of switching elements forming the converter.

At this time, the converter 30 preferably corrects (e.g., by performing subtraction of) the resistance value by using the median (1.5Ω in the example in FIG. 12) of the switching resistance of the switching elements 3201 to 3212 as a correction value, as illustrated in FIG. 12. The resistance value (combined series resistance value) converted by the converter 30 is output to the connection unit 50.

The power supply unit (i.e., the power supply circuit) 45 includes a battery 6 and supplies power to the radio communication unit 10, the information processing unit 20, the converter 30, and other components. The power supply controller 40 has a timer that measures time elapsed after disappearance of operation input, input and receiving of digital data, or the like to prevent the power supply switch 71 from being forgot to be turned off. After the elapse of a predetermined time (for example, ten minutes) after the disappearance of operation input, input and receiving of digital data, or the like, the power supply controller 40 outputs, to the power supply unit 45, a power-off signal for turning off the power supply unit 45.

The connection unit 50 is connectable through wire to the external biological information monitor (e.g., a bedside monitor) 800 and outputs, to the biological information monitor 800, the biological information based on the analog data converted by the converter 30 (for example, the combined series resistance value). A monaural phone plug with φ6.3 mm used for, for example, YSI400 series thermistor probes is preferably used for the connection unit 50. Aa terminal or a connector conforming to the same standard (of the same type) as that for the terminal or the connector of the applied wired biological information monitor 800 is thus used for the connection unit 50. It is also noted that as described above, the connection unit 50 is provided on an end portion of the body part 3 in such a manner as to protrude therefrom.

To prevent an interference with a different conversion adapter 1 or a different medical apparatus plug and to see the presentation part 60 easily (to increase visibility), the connection unit 50 may be provided with a hinge on the proximal end portion (i.e., the attaching portion) of the connection unit 50 as illustrated in FIG. 13, according to an exemplary aspect, and, thus, may be rotatable (e.g., rockable) with the hinge serving as a rotation shaft (rocking shaft), which is an example of a first modification of the exemplary embodiment. In addition, as illustrated in FIG. 14, a configuration in which an L-shaped plug (connection unit) 50 is connected to the tip end portion of a cable 51 may be employed (a second modification). Further, as illustrated in FIG. 15, a configuration in which a linear plug (connection unit) 50 is connected to the tip end portion of the cable 51 may also be employed (a third modification). It is noted that in the configuration illustrated in FIG. 14 (the same holds true for FIG. 19 to be described later) (the second modification of the exemplary embodiment), for example, making variable an angle between the L-shaped plug (connection unit) 50 of the body part 3 and the presentation part 60 (location position) enables improvement in display visibility and installation causing the directivity of a built-in antenna to be advantageous to the biological sensor 700 outside the conversion adapter 1.

Figure 19:
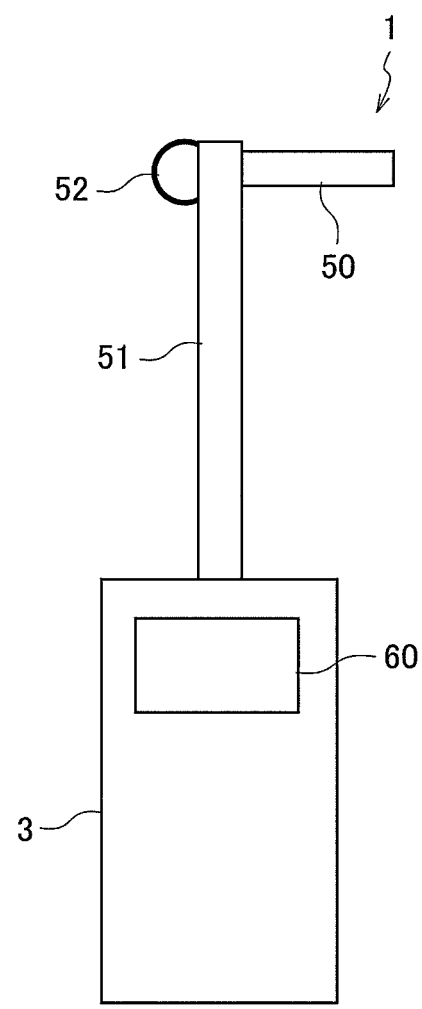
FIG. 19 is a schematic view illustrating a first example of a fixing member.
Figure 20:
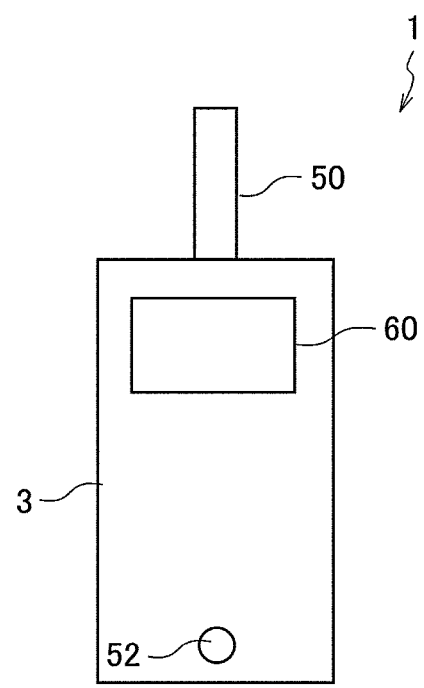
FIG. 20 is a schematic view illustrating a second example of the fixing member.
Figure 21:
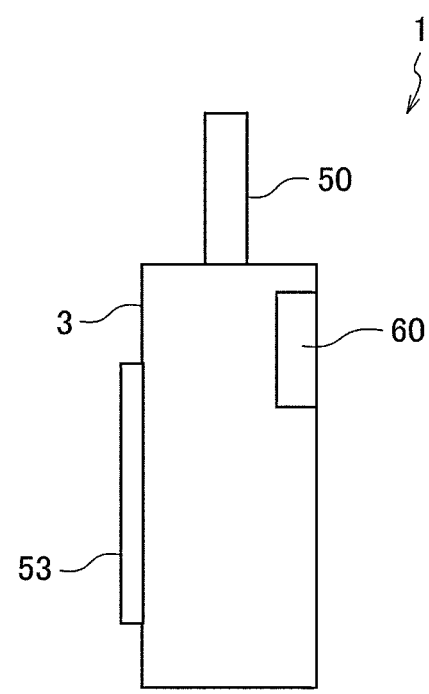
FIG. 21 is a schematic view illustrating a third example of the fixing member.
Figure 22:
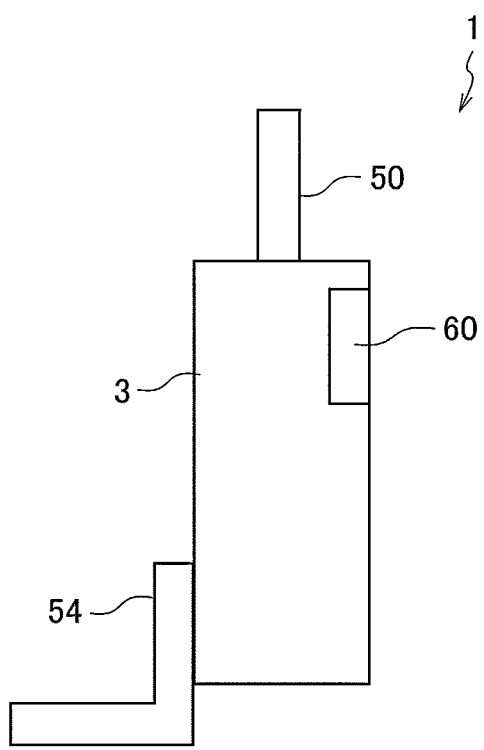
FIG. 22 is a schematic view illustrating a fourth example of the fixing member.

Since the conversion adapter 1 is fixed, for example, at the time or the like of connecting a cable extension, the cable 51 is preferably provided with a strap ring 52 as illustrated in FIG. 19. As illustrated in FIG. 20, the body part 3 may also be provided with the strap ring 52. As illustrated in FIG. 21, a configuration in which the body part 3 is fixed with a hook-and-loop fastener or double-sided tape 53 may also be employed. Further, as illustrated in FIG. 22, a configuration in which the body part 3 is fixed with an L-shaped member (attaching member) 54 may also be employed.

In the configuration as described above, the biological information based on the digital data wirelessly transmitted from the external biological sensor 700 is received, and the received biological information undergoes the data processing and is converted to the analog data conforming to the external biological information monitor (e.g., the bedside monitor) 800. The analog data is output through wire by using the connection unit 50. The biological information monitor 800 connected to the biological sensor 700 through wire can be used simply and at low cost as a wireless biological information monitor, that is, the wireless capability can be added.

According to this exemplary embodiment, the conversion adapter 1 includes the body part 3, the power supply unit 45, and the operation input 7, and thus the operation input 7 can be operated, and the connection unit 50 can be inserted or remove, with the body part 3 in a hand. In addition, since the conversion adapter 1 includes its own power supply (i.e., battery 6), power can be ensured without connection to the biological information monitor 800, and verification and the like of various pieces of information can also be performed in the non-connection state. Accordingly, it is considered that operability is deteriorated in the state of the connection to the biological information monitor 800; however, the operability is not deteriorated because standalone operation is available. That is, the conversion adapter 1 can be operated standalone, that is, in the state without the connection to the biological information monitor 800, without the operability deterioration.

As described in detail above, this embodiment enables the biological information monitor (e.g., the bedside monitor) 800 connected to the biological sensor 700 through wire to be used simply and at low cost as a wireless biological information monitor 800 (that is, the wireless capability to be added) and to be operated standalone, that is, in a state without connection to the biological information monitor, without operability deterioration.

In general, it is noted that the exemplary embodiment of the present invention has heretofore been described. However, the present invention is not limited to the exemplary embodiment above, and various modifications may be made thereto. For example, in the embodiment above, the case where the temperature sensors are used as the biological sensor 700 has been described as an example, but a different biological sensor may also be used instead of the sensors. The type of the algorithmic process is not limited to that in the embodiment above. A configuration in which a process other than the calibration and the deep-body temperature estimation may thus be employed.

REFERENCE SIGNS LIST

1 conversion adapter
3 body part
3*a* upper case
3*b* lower case
3*c* back lid (opening and closing part)
5 circuit board
5*a* through-hole
6 battery 7 operation input
71 power supply switch
71a movable switch part
71b switch cover
72 communication switch
10 radio communication unit
20 information processing unit
30 converter
3101 to 3111 resistor
3201 to 3212 switching element
40 power supply controller
45 power supply unit (power supply circuit)
50 connection unit
51 cable
52 strap ring
53 hook-and-loop fastener or double-sided tape
54 L-shaped member (fixing member)
60 presentation part
700 biological sensor
800 biological information monitor

The invention claimed is:

1. A conversion adapter comprising:
a communication unit configured to receive biological information transmitted from an external apparatus by wireless communication;
a converter configured to convert the biological information received by the communication unit to biological information processible by an external biological-information processing apparatus;
a connection unit configured to be connected to the external biological-information processing apparatus and configured to output the biological information converted by the converter to the biological-information processing apparatus;
a power supply unit configured to supply power to the communication unit and the converter;
an operation input configured to receive an operation from a user; and
a main body provided with the connection unit and the operation input,
wherein the communication unit is disposed inside the main body on a different end portion side than the connection unit.

2. The conversion adapter according to claim 1, wherein the communication unit is configured to wirelessly receive the biological information transmitted from an external biological sensor by using radio communication and further configured to transmit information to at least one of the biological sensor and an external medical apparatus by using radio communication.

3. The conversion adapter according to claim 1, wherein the connection unit is provided on end portion side of the main body that opposes the end portion side on which the communication unit is disposed.

4. The conversion adapter according to claim 1, wherein the operation input includes a plurality of operation switches that are each different in at least one of an operation method, a size, and a shape.

5. The conversion adapter according to claim 4, wherein at least part of an outer surface of the main body comprises a concave shape.

6. The conversion adapter according to claim 5, wherein the operation input is disposed on the concave shape of the outer surface.

7. The conversion adapter according to claim 4, further comprising:

a circuit board disposed inside the main body and having a through-hole that extends in a thickness direction of the circuit board; and
a switch cover that includes a pair of protruding portions parallel to each other and that is attached to a top surface of the main body to slide freely.

8. The conversion adapter according to claim 7,
wherein one operation switch of the plurality of operation switches is mounted on the circuit board such that a slidable movable part protrudes parallel to a main surface of the circuit board, and
wherein the switch cover is attached such that the pair of protruding portions extend in a direction perpendicular to the main surface of the circuit board and protrude through the through-hole in the circuit board, such that tip ends of the pair of protruding portions abut on an inner side of a lower surface of the main body, and such that the movable part of the one operation switch is engaged between the pair of protruding portions.

9. The conversion adapter according to claim 1,
wherein the main body has an operable and closable opening and closing part, and
wherein opening and closing directions of the opening and closing part are different from inserting and removing directions of the connection unit.

10. The conversion adapter according to claim 1, further comprising a presentation part configured to present at least one of the biological information and operation information regarding the operation input.

11. The conversion adapter according to claim 1, wherein an exterior of the main body comprises a crystalline material.

12. The conversion adapter according to claim 1, further comprising a fixing member configured to fix the conversion adapter.

13. The conversion adapter according to claim 1, further comprising an information processing unit configured to convert the biological information to a digital value that corresponds to an analog amount of the biological information received by the communication unit and further configured to provide the digital value of the biological information to the converter.

14. The conversion adapter according to claim 13, wherein the information processing unit is configured to convert the biological information based on one of a transformation or a reference table.

15. The conversion adapter according to claim 13, wherein the converter is configured to convert the digital value of the biological information to a resistance value that corresponds to a resistance value of the analog amount received by the communication unit.

16. The conversion adapter according to claim 15, wherein the converter comprises a plurality of resistors connected in series and switching elements that are respectively connected in parallel to the plurality of resistors and that respectively turn on and off the plurality of resistors.

17. The conversion adapter according to claim 16, wherein the converter is configured to obtain the resistance value to match a combined series resistance value by turning on and off of the switching elements to achieve an obtained combination of the plurality of resistors.

18. The conversion adapter according to claim 1, wherein the main body includes an upper case, a lower case, and an operable and closable back lid, with the operation input provided on the upper surface of the main body.

19. The conversion adapter according to claim 1, wherein the connection unit comprises a hinge on a proximal end of the end portion side of the main body, such that the connection unit is rotatable.

* * * * *